United States Patent [19]

Arnold

[11] Patent Number: 5,703,259
[45] Date of Patent: *Dec. 30, 1997

[54] METHOD FOR THE PREPARATION OF PURE CARBOXYETHYL GERMANIUM SESQUIOXIDE

[76] Inventor: Michael J. Arnold, 4521 Campus Dr., Suite 225, Irvine, Calif. 92715

[*] Notice: The term of this patent shall not extend beyond the expiration date of Pat. No. 5,386,046.

[21] Appl. No.: 577,307

[22] Filed: Dec. 22, 1995

Related U.S. Application Data

[63] Continuation-in-part of Ser. No. 204,548, Mar. 2, 1994, Pat. No. 5,386,046, and a continuation-in-part of Ser. No. 381,343, Jan. 31, 1995, Pat. No. 5,504,225.

[51] Int. Cl.$^6$ .................................................. C07F 7/30
[52] U.S. Cl. ............................... 556/89; 556/87; 556/105
[58] Field of Search ............................ 556/87, 89, 105

[56] References Cited

U.S. PATENT DOCUMENTS

| | | | |
|---|---|---|---|
| 3,793,455 | 2/1974 | Asai et al. | 424/287 |
| 4,066,678 | 1/1978 | Sato et al. | 260/429 R |
| 4,473,581 | 9/1984 | Ishida et al. | 424/287 |
| 4,898,882 | 2/1990 | Nagahama et al. | 514/492 |
| 4,956,272 | 9/1990 | Kakimoto et al. | 435/1 |
| 4,973,553 | 11/1990 | Miyao et al. | 435/206 |
| 5,386,046 | 1/1995 | Arnold | 556/89 |
| 5,550,266 | 8/1996 | Arnold | 556/89 |

*Primary Examiner*—Porfirio Nazario-Gonzalez

[57] ABSTRACT

A synthetic method for generating pure carboxyethyl germanium sesquioxide in the absence of toxic impurities. In the method germanium dioxide and metallic germanium are not used as starting materials. The method involves steps which ensure (a) absence of any residual germanium tetrachloride to ensure none is available to form germanium dioxide, (b) removal of any germanium dioxide, (c) removal of any germanium tetrachloride later produced from any germanium dioxide and (d) final removal of any germanium dioxide. In an alternative method, intermediate TPA is prepared by direct precipitation from a concentrated solution with a halogenated solvent preferably dichloromethane when poured into a non-polar alkyl solvent preferably hexane at ambient temperature and then converted to carboxyethyl germanium sesquioxide.

11 Claims, No Drawings

METHOD FOR THE PREPARATION OF PURE CARBOXYETHYL GERMANIUM SESQUIOXIDE

RELATED APPLICATIONS

This application is a continuation-in-part of U.S. patent application Ser. No. 08/204,548 filed on 02 Mar. 1994, now U.S. Pat. No. 5,386,046 issued Jan. 31, 1995 and of U.S. patent application Ser. No. 08/381,343 filed on 31 Jan. 1995, now U.S. Pat. No. 5,504,225 issued Aug. 27, 1996, the contents of which are incorporated herein by this reference.

BACKGROUND

1. Field of the Invention

The present invention relates to a synthetic method for generating pure carboxyethyl germanium sesquioxide, and in particular to a chemical method for synthesizing carboxyethyl germanium sesquioxide that yields the carboxyethyl germanium sesquioxide without trace amounts of germanium dioxide or metallic germanium.

2. Background of the Invention

Carboxyethyl germanium sesquioxide (organic germanium) has been shown to have chemotherapeutic value. Nakao Ishida, et. al., U.S. Pat. No. 4,473,581 teach that carboxyethyl germanium sesquioxide can induce interferon production in humans. Nagahama teaches in U.S. Pat. No. 4,898,882 that carboxyethyl germanium sesquioxide can provide the human body resistance against the common cold. Asai in U.S. Pat. No. 3,793,455 describes the use of carboxyethyl germanium sesquioxide as an agent for treatment of hypertension. Although carboxyethyl germanium sesquioxide is a well known compound, its molecular structure has been shown to be dependent on the synthetic method employed.

For use as a chemotherapeutic agent, or as a food supplement, it is required that carboxyethyl germanium sesquioxide be pure, free of unwanted and potentially lethal contaminants germanium dioxide and metallic germanium. Many known methods for synthesizing carboxyethyl germanium sesquioxide provide for the production of germanium sesquioxide contaminated with trace amounts of metallic germanium, or germanium dioxide, since these are used as the starting materials. Trichlorogermanium acrylate moieties (trichlorogermanium acroyl chlorides, trichlorogermanium acrylic acids, trichlorogermanium acrolein and trichlorogermanium alkyl acrylates) are the key intermediates common to such known synthetic routes. Entries described by the prior art to the trichlorogermanium acrylate intermediates, utilize methods that require either oxidation of metallic germanium with hydrochloric acid, or reduction of germanium dioxide and, hence, the probability of the presence of trace amounts of unreacted starting material (metallic germanium or germanium dioxide) in the product is significant.

The present invention does not start with either metallic germanium or germanium dioxide, but rather starts with germanium tetrachloride.

SUMMARY OF THE INVENTION

Accordingly, a major object of the present invention is the provision of a synthetic method that is devoid of the aforementioned drawbacks which to date have characterized this art.

It is the primary object of the present invention to provide a method whereby carboxyethyl germanium sesquioxide can be prepared without contamination from metallic germanium or germanium dioxide.

It is another object of the present invention to provide a method for the production of a carboxyethyl germanium sesquioxide molecular species that is completely non toxic to the human body.

It is another object of the present to provide a method for the production of a carboxyethyl germanium sesquioxide molecular species that has an $LD_{50}$ value of at least 5 g/Kg.

The present method involves the isolation and purification of the intermediate trichlorogermane propionic acid (hereafter referred to as TPA). In this method reaction of germanium tetrachloride in the presence of acrylic acid takes place under ambient conditions to form a mixture of polymeric material and TPA. This mixture is then depolymerized with concentrated hydrochloric acid to form a crude TPA reaction product, which is then recrystallized to a pure TPA form. The pure TPA is then hydrolyzed and reacted with sulfuric acid to form carboxyethyl germanium sesquioxide.

In an alternative method the recrystallization step is omitted. Instead, after the mixture is depolymerized with concentrated hydrochloric acid to form a crude TPA reaction product as a white amorphous solid, it is directly hydrolyzed and acidified to form carboxyethyl germanium sesquioxide.

In another alternative, process TPA in crude form is mixed with dichloromethane, as in the first process; then the major amount of dichloromethane is removed to give a liqueur of TPA and the remaining dichloromethane. This is then mixed with a non-polar alkyl solvent, such as hexane at ambient temperature to precipitate crystals of pure TPA. With certain minor changes the process then proceeds to form carboxyethyl germanium sesquioxide.

DETAILED DESCRIPTION OF THE INVENTION

The method of the invention involves the steps of forming from the starting material of germanium tetrachloride, an intermediate material, trichlorogermane propionic acid, isolating and purifying the trichlorogermane propionic acid and converting the TPA by hydrolysis to carboxyethyl germanium sesquioxide.

The specific steps of the process are described as follows:

a first mixture is obtained by reacting germanium tetrachloride with tetraethyl disiloxane and acrylic acid. This first mixture consists essentially of trichlorogermane propionic acid (TPA), a polymer and volatile by-products. The reaction profile is:

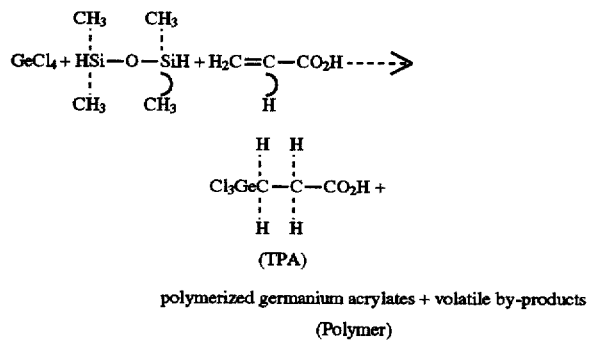

polymerized germanium acrylates + volatile by-products (Polymer)

The first mixture is subjected to vacuum distillation to remove the volatiles. This results in a second mixture which consists essentially of TPA plus the polymerized germanium acrylate (hereafter referred to as "polymer"). The chemical profile of this step is:

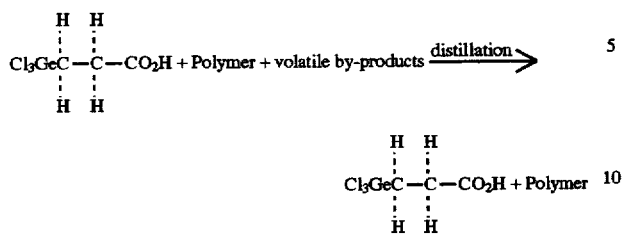

The second mixture is reacted with hydrochloric acid in sufficient amount, preferably in excess, to completely react with the polymer for depolymerization, that is to convert the polymer to TPA providing a third mixture consisting essentially of TPA and hydrochloric acid. That is, it is a heterogeneous mixture of white solid TPA and aqueous HCL (conc). The reaction profile is:

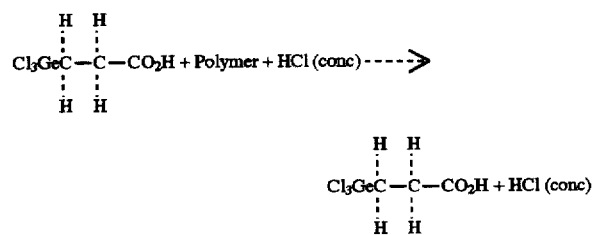

The third mixture is subjected to solvent extraction to separate the hydrochloric acid from the TPA and provide a fourth mixture consisting essentially of TPA and extraction solvent. The preferred solvent is a sufficient amount, preferably in excess, of a halogenated solvent, specifically dichloromethane being most preferred. Chloroform and carbotetrachloride might also work. The reaction profile is:

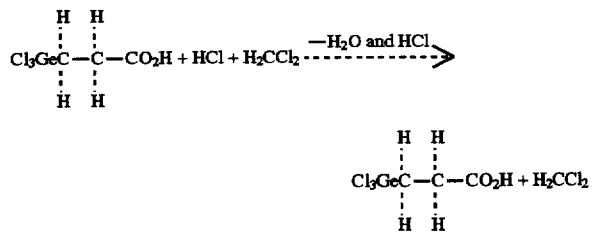

The fourth mixture is subjected to vacuum distillation to remove the solvent ($H_2CCl_2$) resulting in a crude reaction product, consisting essentially of TPA. That is, the TPA is in a form or mixture presumed to be insufficiently pure. The reaction profile is:

Next the crude TPA reaction product is purified and converted to carboxyethyl germanium sesquioxide by the following steps:

The crude TPA reaction product is dissolved in a minimal amount of boiling non-polar alkyl solvent, preferably hexane, to form upon cooling, high purity crystals of TPA. The hexane is removed and the resulting crystals are washed successively with hexane in order to yield fine pure crystals of TPA. The reaction profile is:

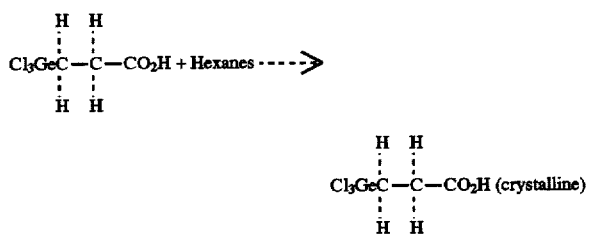

This results in pure crystals of TPA.

Next the pure TPA crystals are reacted in a sufficient amount, preferably in excess, of ammonium hydroxide, to form a fifth mixture consisting of hydrolyzed TPA. Slow addition of concentrated sulfuric acid yields carboxyethyl germanium sesquioxide. The chemical profile is:

Fifth mixture+$H_2SO_4$ (conc)→$Ge_2C_6H_{10}O_7$

A one-pot synthesis of analytically pure organic germanium is described below.

To a 2 L round bottom flask purged with argon was added successively: germanium tetrachloride (200 g [0.9346 mol]), tetraethyl disiloxane (125 g[0.93 mol]), and acrylic acid (70.0 g[0.97 mol]). The reaction flask was purged with argon then sealed by placement of a ground glass stopper with a teflon sleeve and secured via teflon tape. The slightly cloudy mixture changed to a clear, colorless homogeneous solution within about 2 hours, and this was stirred for seven days at ambient temperature. The volatile components were removed via vacuum (0.5 to 5 mmHg) while the product mixture was heated to an internal temperature of 70°–C.–80° C., where it was a homogeneous, clear and colorless viscous solution (melt). Evacuation was continued until no more distillate was observed (ca. 2 hours). This was cooled to an ambient temperature to yield a white amorphous solid. To this was added 950 mL of concentrated HCl. The resulting heterogeneous mixture was warmed to an internal temperature of 60° C.–70° C., and stirred for four hours. The cooled mixture was extracted 3 times with 500 mL of dichloromethane. The combined extracts were evaporated under reduced pressure via rotary evaporator to give a white amorphous solid. This was dissolved in ca. 1 L boiling hexane (until a clear colorless homogeneous hot solution was obtained), and let cool gently to ambient temperature. The product, trichlorogermane propionic acid, was isolated via suction filtration, washed once with hexane to give fine prisms, mp 75° C.–79° C. (a range of mp 75° C.–90° C. would be acceptable). This was immediately taken up (vigorous reaction), with careful addition of 850 mL of ammonium hydroxide (29% ammonia). The resulting turbid mixture was stirred for 4 days at ambient temperature (the mixture changes to a clear, colorless homogeneous solution within 3 hours). To this homogeneous solution was added dropwise over two hours through a reflux condenser 400 mL of concentrated sulfuric acid. NOTE: This is a very vigorous reaction and should be handled with extreme care. A white precipitate formed after addition of ca. 375 mL of acid. The pot was stirred for 48 hours, and then the white solid was isolated via suction filtration, washed successively with 2×150 mL water, 1×150 mL acetone, and 1×200 mL of dimethyl ether, then this brilliant white solid was air dried overnight, and then taken up with 150 mL hot water (~80° C.), when it was stirred for about 1 hour, then cooled to ambient temperature and filtered to give a white solid. This was washed successively with 2×150 mL of water, 1×150 mL acetone and 1×150 diethyl ether to yield 78.84 g (50%) of analytically pure carboxyethyl germanium sesquioxide.

In an alternative method, the same steps as described above are taken, except that the recrystallization step is omitted. In this alternative method, after the mixture is depolymerized with concentrated hydrochloric acid to form TPA and the hydrochloric acid removed, and the resulting mixture, which is referred to above as the fourth mixture is cleansed of solvent it is then directly hydrolyzed and acidified to form carboxyethyl germanium sesquioxide.

An example of this alternative process follows. To a 50 L glass reactor was added successively: 7.2 Kg germanium tetrachloride, 5.3 Kg tetramethyl disiloxane, and 2.32 Kg of acrylic acid. The resulting mixture was stirred for 5 days forming TPA (trichlorogermane propionic acid) as a product. Volatile components were removed via vacuum distillation while the TPA product was heated to an internal temperature of 75° C.—80° C., where it was a homogeneous, clear and colorless viscous melt. Distillation is continued until no more distillate appears. The product was then cooled to ambient temperature yielding a white amorphous solid of TPA. To this was added 35 L of concentrated HCl. The resulting heterogeneous mixture was warmed to an internal temperature of 60° C.–70° C., and stirred for four hours and allowed to cool. The cooled mixture was extracted 3 times with 25 L of dichloromethane. The dichloromethane was removed with vacuum distillation at 40° C. to give a white amorphous solid. The white amorphous solid, crude TPA, was then hydrolyzed to carboxyethyl germanium sesquioxide. This was immediately taken up (vigorous reaction), with careful addition of 30 L of ammonium hydroxide (29% ammonia). The resulting mixture was stirred for 4 days at ambient temperature. To this, 14.4 L of concentrated sulfuric acid was added dropwise over two hours through a reflux condenser at a temperature not greater than 25° C. producing a white solid of carboxyethyl germanium sesquioxide. The white solid was isolated via suction filtration, washed successively with 2×5.4 L acetone, and 2×5.4 L of dimethyl ether, then the resulting brilliant white solid was air dried overnight, and then taken up with 9 L of hot water (~80° C.), and stirred for two hours, cooled and filtered to give a white solid which was washed twice in 5.4 L t-botyl methyl ether to yield carboxyethyl germanium sesquioxide.

In the production of organic germanium for human consumption such as a food supplement there is concern about the possible presence of metallic germanium and germanium dioxide. In the present invention, including either of the methods described above, there can be no metallic germanium because the starting materials and methods do not have the potential for producing any metallic germanium. In respect of germanium dioxide, the first procedure, in particular the recrystallization step will eliminate any potential for the presence of germanium dioxide. In respect of the second method, the procedures effectively eliminate any reasonable possibility of the presence of germanium dioxide. The basis for this conclusion is now explained. Any germanium dioxide found in the product as synthesized in this method would have as its precursor the germanium tetrachloride. In the initial reaction of germanium tetrachloride with tetramethyl disiloxane and acrylic acid it is theoretically possible that there remains unreacted germanium tetrachloride (considered to be part of the volatile by-products) which would have the theoretical potential to hydrolyze to form germanium dioxide. Thus there is a theoretical possibility of the presence of germanium dioxide, which is a solid.

The next step of vacuum distillation would remove any remaining unreacted germanium tetrachloride. Also, any germanium dioxide in the aqueous phase is removed and discarded as noted this is done three times for thoroughness.

The next reaction, with hydrochloric acid would convert any then present germanium dioxide to germanium tetrachloride.

The next step of solvent extraction with dichloromethane will allow any germanium dioxide in the organic to be observed (as a solid) and in the laboratory testing, none has been observed (germanium dioxide is insoluble in dichloromethane). Therefore it is concluded that no germanium dioxide is present in the organic phase.

The next step of vacuum distillation would remove any remaining germanium tetrachloride that had been formed, thus precluding any subsequent formation of germanium dioxide.

It can be appreciated that in general there is only the barest theoretical possibility of the formation of germanium dioxide or its presence in the end product. With the steps employed even this possibility is obviated. Therefore this method is seen as providing a resulting product of sufficient purity for human consumption.

As compared to the first procedure, the second procedure has at least two important advantages. The first advantage refers to avoiding the use of hexane. Hexane is a volatile organic contaminant (VOC); an atmospheric contaminant. It is also dangerously explosive. Therefore its elimination is salutary.

Secondly, the recrystallization step adds a substantial amount of time and labor to the manufacturing process; its elimination providing the concomitant benefits.

An another preferred embodiment of the invention, a third procedure is conveniently described as a variation of the first procedure, although as will be seen it also is a variant of the alternate procedure. Referring to the first procedure, crude TPA is isolated as an extract from mixture with dichloromethane by vacuum distillation (this is also done in the alternate procedure).

However, in this third procedure, the fourth mixture is subjected to vacuum distillation to remove most of the solvent ($H_2CCl_2$) resulting in a crude reaction mixture, a concentrated mixture, consisting essentially of TPA and dichloromethane. That is, the TPA is in a mixture with dichloromethane, for example in which only 80% of the dichloromethane has been removed. The reaction profile is:

Fourth mixture $\xrightarrow{\text{partial vacuum distillation}}$

Crude TPA + residual dichloromethane

This defines, for this embodiment, a fifth mixture, a concentrated mixture of TPA and a minor amount (of the original amount) of dichloromethane. That is, less than half of the original amount of dichloromethane is left.

The range of content of the dichloromethane in the mixture is acceptably from 3% to 60%, preferably 5% to 55% and most preferably 10% to 50%.

Note that other methods of distillation could be used in this example at this step to result in the concentrated mixture.

The crude TPA mixture (the fifth mixture) is poured into an excess amount of non-polar alkyl solvent, preferably hexane, at ambient temperature, to immediately form crystals of pure TPA. The solvent mixture of hexane and dichloromenthane is removed by filtration and the resulting crystals are washed successively with hexane, preferably at ambient temperatures, in order to yield pure TPA. The reaction profile is:

Fifth mixture→Cl₃GeC2H4CO₂H (TPA)

This results in pure crystals of TPA.

By this process pure crystals of TPA are produced without the danger and expense of boiling on hot hexanes. Instead, concentrated TPA is in mixture with residual dichloromethane as a concentrated mixture or heterogeneous mixture. The concentrated mixture (or mixture) is treated with excess ambient temperature hexane which forms the TPA crystals as a precipitate. Use of excess hexane ensures high yield of pure TPA. Impurities are soluble in the dichloromethane and hexane solvent mixture and therefore the impurities stay in solution. But, TPA is almost completely insoluble in the solvent mixture. Thus, there is high confidence that the resulting TPA is very pure with no appreciable contamination from impurities. This procedure is analogous to the first procedure, with equivalent results in respect of the purity of the resulting TPA but without the danger and expense of boiling hexanes. The TPA crystals are filtered and hydrolyzed with ammonia hydroxide. Then sulfuric acid is slowly added at chilled temperature such as from about 5° C. to 25° C. to yield carboxyethyl germanium sesquioxide. The resulting white solid is isolated by filtration, washed successively with acetone and diethyl ether (or t-butyl methyl ether (a safer solvent)) dried, taken up with hot water and then cooled and filtered.

An example of this alternative process follows. To a 50 L glass reactor was added successively: 7.2 Kg germanium tetrachloride, 5.3 Kg tetramethyl disiloxane, and 2.3y Kg of acrylic acid. The resulting mixture was stirred for 5 days forming TPA (trichlorogermane propionic acid) as a product. Volatile components were removed via vacuum distillation while the TPA product was heated to an internal temperature of 75° C.–80° C., where it was a homogeneous, clear and colorless viscous melt. Distillation is continued until no more distillate appears. The product was then cooled to ambient temperature yielding a white amorphous solid. To this was added 35 L of concentrated HCL. The resulting heterogeneous mixture was warmed to an internal temperature of 60° C.–70° C. and stirred for four hours and allowed to cool. The cooled mixture was extracted 3 times with 25 L of dichloromethane. Instead of removing all 75 L of the dichloromethane as in the previous examples, between about 50 L–70 L of the dichloromethane was removed with vacuum distillation at between about 25° C. to 40° C. to give a clear, colorless concentrated mixture. This concentrated mixture was poured into about 50 L of hexane at ambient temperature. Fine crystals of TPA appeared as a precipitant and the solution was let stand 4–8 hours. The solid is filtered. Then the solid is slowly added to 30 L of ammonium hydroxide (28–35%). To this, 21.6 L of 75% sulfuric acid was added over 2 hours with the temperature maintained below 25° C. The white solid was isolated via suction filtration, washed successively with 2×5.4 L acetone, and 2×5.4 L of diethyl ether, then the resulting brilliant white solid was air dried overnight to give a white solid. This white solid was then taken up in 9 L of hot water (~80° C.) and stirred for 2 hours, cooled and filtered to give a white solid, which was washed twice in 5.4 L water, then once with 5.4 L t-butyl methyl ether.

In use carboxyethyl germanium sesquioxide is believed to have beneficial effects for humans. For example it is believed to stimulate the production of interferon. With regular use a 100 mg/day dosage is appropriate. With flu symptoms 1,000 mg/day has been recommended. It is a stable compound and may be combined with other energy source type supplements. It is compatible with commonly used excipient such as maltodextrin and microcrystalline cellulose.

An exemplary mixture of a food supplement using organic germanium is:

| | |
|---|---|
| Pangamic acid | 50 mg. |
| Organic germanium | 25 mg. |
| Co Enzyme Q10 | 25 mg. |
| Vitamin A | 1,250 I.U. |
| Vitamin E | 100 I.U. |
| Vitamin D | 7.5 I.U. |
| Vitamin K | 125 mg. |

Although particular embodiments of the invention have been described and illustrated herein, it is recognized that modifications and variations may readily occur to those skilled in the art, and consequently it is intended that the claims be interpreted to cover such modifications and equivalents.

I claim:

1. A method of preparing organic germanium in the absence of any toxic level of germanium dioxide or metallic germanium composing;

preparing TPA as a crude reaction product from germanium tetrachloride including a step of solvent extraction using a halogenated solvent;

removing all but a minor amount of the original amount of halogenated solvent leaving a concentrated mixture of the TPA in mixture with a remaining minor amount of halogenated solvent;

mixing said concentrated mixture with an excess amount of a non-polar alkyl solvent at ambient temperature to form high purity crystals of TPA;

isolating the high purity crystals of TPA from the non-polar alkyl solvent;

converting the high purity crystals of TPA to carboxyethyl germanium sesquioxide.

2. The method of claim 1 wherein said halogenated solvent is between about 3% to 60% of said concentrated mixture.

3. The method of claim 1 wherein said halogenated solvent is between about 5% to 55% of said concentrated mixture.

4. The method of claim 1 wherein said halogenated solvent is between about 10% to 50% of said concentrated mixture.

5. The method of claim 1 wherein said halogenated solvent is dichloromethane.

6. The method of claim 5 wherein said dichloromethane is between about 3% to 60% of said concentrated mixture.

7. The method of claim 5 wherein said dichloromethane is between about 5% to 55% of said concentrated mixture.

8. The method of claim 5 wherein said dichloromethane is between about 10% to 50% of said concentrated mixture.

9. The method of claim 1 wherein said non-polar alkyl solvent is hexane.

10. The method of claim 9 wherein said halogenated solvent is dichloromethane.

11. The method of claim 1 wherein said isolating step comprises;

hydrolyzing the high purity crystals of TPA in ammonium hydroxide and;

reacting the halogenated TPA with sulfuric acid to yield carboxyethyl germanium sesquioxide.

* * * * *

UNITED STATES PATENT AND TRADEMARK OFFICE
CERTIFICATE OF CORRECTION

PATENT NO. : 5,703,259
DATED : December 30, 1997
INVENTOR(S) : Michael J. Arnold It is certified that error appears in the above-identified patent and that said Letters Patent is hereby corrected as shown below:

Title page, item [73], Assignee: should read--
    Viva America Marketing, Inc.,
1239 Victoria Street, Costa Mesa, California 92627.

Signed and Sealed this

Thirtieth Day of June, 1998

Attest:

BRUCE LEHMAN

Attesting Officer      *Commissioner of Patents and Trademarks*